(12) United States Patent
Lubitz

(10) Patent No.: US 8,568,738 B2
(45) Date of Patent: Oct. 29, 2013

(54) VIRUS-MODIFIED BACTERIA GHOSTS

(76) Inventor: Werner Lubitz, Klosterneuburg/Kritzendorf (AT)

( * ) Notice: Subject to any disclaimer, the term of this patent is extended or adjusted under 35 U.S.C. 154(b) by 350 days.

(21) Appl. No.: 12/670,525

(22) PCT Filed: Jul. 28, 2008

(86) PCT No.: PCT/EP2008/006207
§ 371 (c)(1), (2), (4) Date: Jan. 25, 2010

(87) PCT Pub. No.: WO2009/015852
PCT Pub. Date: Feb. 5, 2009

(65) Prior Publication Data
US 2010/0203082 A1 Aug. 12, 2010

(30) Foreign Application Priority Data

Jul. 27, 2007 (EP) .................................. 07014799

(51) Int. Cl.
| | |
|---|---|
| *A61K 39/295* | (2006.01) |
| *A61K 39/12* | (2006.01) |
| *A61K 39/02* | (2006.01) |
| *A61K 45/00* | (2006.01) |
| *A01N 63/00* | (2006.01) |

(52) U.S. Cl.
USPC ................. 424/201.1; 424/204.1; 424/234.1; 424/282.1; 424/93.4; 424/93.6

(58) Field of Classification Search
None
See application file for complete search history.

(56) References Cited

FOREIGN PATENT DOCUMENTS

| | | |
|---|---|---|
| DE | 199 03 345 A1 | 8/2000 |
| WO | 00/53163 A | 9/2000 |

OTHER PUBLICATIONS

Lubitz et al., Lysis of *Escherichia coli* after Infection with ix174 Depends on the Regulation of the Cellular Autolytic System, 1984, Journal of General Microbiology, vol. 130, pp. 1079-1087.*
Paukner et al., Sealed Bacterial Ghosts—Novel Targeting Vehicles for Advanced Drug Delivery of Water-soluble Substances, 2003, Journal of Drug Targeting, vol. 11, No. 3, pp. 151-161.*
Mayr et al., "Bacterial ghosts as antigen delivery vehicles", Advanced Drug Delivery Reviews, vol. 57,No. 9, Jun. 17, 2005, pp. 1381-1391.

* cited by examiner

*Primary Examiner* — Benjamin P Blumel
(74) *Attorney, Agent, or Firm* — Rothwell, Figg, Ernst & Manbeck, P.C.

(57) ABSTRACT

The invention relates to virus-modified bacteria ghosts and the use thereof, for example, as carrier and targeting vehicles for active ingredients.

19 Claims, No Drawings

VIRUS-MODIFIED BACTERIA GHOSTS

CROSS REFERENCE TO RELATED APPLICATION

This application is a 35 U.S.C. 371 National Phase Entry Application from PCT/EP2008/006207, filed Jul. 28, 2008, which claims the benefit of European Patent Application No. 07014799.6 filed on Jul. 27, 2007, the disclosure of which is incorporated herein in its entirety by reference.

The invention relates to virus-modified bacterial ghosts (BGs) and the use thereof, for example as vaccine particles, carrier and targeting vehicles for active ingredients and for applications in nano-technology. Bacterial viruses are also referred to as bacteriophages (Bph) or phages.

Empty bacterial envelopes, so-called BGs, can be prepared in gram-negative bacteria by controlled, heterologous expression of gene which causes partial lysis of the cell membrane (EP-A-0 291 021). An example of such a lytic gene is gene E of the bacteriophage PhiX174, which codes for a polypeptide which inserts into the cell wall complex of gram-negative bacteria and by oligomerization leads to the formation of a trans-membrane tunnel structure through the inner and outer membrane. The internal diameter of this tunnel structure can be 40 to 200 nm or 500 to 1000 nm depending on the lysis conditions. The cytoplasmic material of the cell is released through this tunnel leaving an empty cell envelope with intact morphology. The use of BGs as dead vaccines or adjuvants and the preparation of recombinant BGs which bear heterologous surface proteins in their membrane is described in WO 91/13555 and WO 93/01791.

Furthermore, as described in WO 00/053163, BGs are outstandingly suitable as carrier or targeting vehicles for active ingredients. A first advantage of the BGs consists in that simple administration via the natural infection route of pathogens or by natural receptor recognition of non-pathogenic bacteria such as for example via the respiratory or the gastrointestinal tract or other mucous membranes is possible. This applies also for receptors on plants or the adsorption of bacteria on non-living materials. In addition, the system of active ingredient administration via BGs as carriers provides effective targeting owing to the specificity of the BGs for various types of tissue. Hence the active ingredient is brought with high efficiency to the desired target site, e.g. the relevant potential infection site of the original bacteria, or in general to the desired target site. The advantage of natural bacterial envelopes as vectors can only be achieved with difficulty and unreliably with other administration forms, such as for example liposomes, even with incorporated proteins or ligands.

Since BGs which contain only the desired active ingredient can be prepared, a high loading level and hence high efficiency of the active ingredient can be achieved. In addition, the BGs are a reliable carrier material since these are not viable organisms. Finally, the BGs are products with high immune-stimulatory activity owing to the presence of lipopolysaccharides and peptidoglycans, so that no additional adjuvants have to be added, since the BGs per se produce the adjuvant effect.

Surprisingly, it has been found that BGs can be infected with bacteria-specific viruses, so-called bacteriophages (Bph) and that the resulting Bph-modified BGs are suitable for applications in molecular biology and medicine. Through the Bph infection, the physical and chemical properties of the BGs can be modified. Further, targeting molecules and active ingredients can be enclosed and/or bound into the BGs in this manner.

Hence one subject of the invention is BGs modified with Bph.

A further subject of the invention is the use of BGs modified with Bph in molecular biology and in medical diagnosis and therapy as carrier or/and targeting vehicles for an active ingredient, e.g. as a vaccine or adjuvant, as a nucleic acid vector or for combinatorial applications.

Bph-infected BGs can be obtained by Bph infection of appropriate bacteria before or/and after the E-induced lysis. Preferably, the Bph infection is effected after the bacterial lysis.

For the infection of the BGs, any phages can be used, provided that they are capable of infecting a given bacterial cell. Specific examples of such Bph are Bph of the Styloviridae family, such as for example lambdoid phages, e.g. the Bph lambda specific to *E. coli* and Mu phages, Bph of the Myoviridae family, such as for example even-numbered T phages, e.g. T2, T4 and T6, Bph of the Podoviridae family, such as for example odd-numbered T phages, e.g. T1, T3, T5 and T7, Bph of the Tectiviridae family, e.g. pRD1, Bph of the Cortico-viridae family, e.g. pM2, Bph of the Plasmaviridae family, Bph of the Microviridae family, e.g. PhiX174, filamentous Bph of the Inoviridae family, e.g. fd and M13, which are DNA Bph. Further, RNA Bph, e.g. Bph of the Leviviridae family, e.g. MS2, F2 and Qβ, are also suitable. The infection of the BGs can be effected with one or more Bph species, whereby the Bph adhere to receptor substances of the bacterial outer membrane or/and to cell appendages such as flagellae or pili. Particularly preferably, the Bph are selected from lambdoid Bph, filamentous Bph and Bph of the PhiX174 type.

The Bph-infected BGs can be used for various purposes. Thus in one embodiment of the invention phages which contain one or more heterologous polypeptides, preferably built into the Bph wall, but also optionally in their interior, are used. These heterologous peptides can be selected from recognition polypeptides for cell receptors in order to enable deliberate introduction of the Bph-modified BGs into desired cell types, e.g. cells of the immune system. Moreover, the heterologous polypeptides can also be docking polypeptides for enzymes, antibodies or other polypeptides, e.g. streptavidin. In this manner, further heterologous polypeptides can be deliberately immobilized on the outside of the outer BG membrane. Owing to the often site-specific attachment of the Bph to the bacterial surface or certain bacterial surface structures, such as for example outer membrane proteins, porins, LPS, pili, flagellae or S layers, this type of immobilization has advantages over the direct immobilization of recombinant polypeptides in the BG membrane, which is already known in the state of the art.

Yet another application is Bph display, wherein a population of recombinant phages with combinatorial polypeptides, which express desired DNA sequences, is used. Individual Bph from this population can be identified by binding of the Bph-modified BGs to specific receptors.

Furthermore, BGs which contain a heterologous nucleic acid e.g. therapeutic nucleic acids such as for example nucleic acids for gene therapy, which are preferably present in the form of a chromosomally integrable vector, antisense nucleic acids, therapeutic RNA molecules or nucleic acid vaccines, can also be used.

In addition or/and alternatively, the BG can also contain one or more active ingredients packaged in its interior. The active ingredient can be any active ingredient transportable into the interior of the BG and preferably immobilizable there. Preferably, the active ingredient is selected from pharmacologically active ingredients and labeling substances.

Examples of pharmacologically active ingredients are polypeptides such as for example antibodies, therapeutically active polypeptides such as cytokines, interferons, chemokines, etc., enzymes and immunogenic polypeptides. A further example of active ingredients is nucleic acids, in particular therapeutic nucleic acids, e.g. nucleic acid vaccines, nucleic acids for gene therapy, which are preferably present in the form of a chromosomally integrable vector, antisense nucleic acids or ribozymes. Still further examples of active ingredients are small molecule active ingredients, peptides, hormones, antibiotics, antitumor agents, steroids, immune modulators, etc. The active ingredients can be present in the BGs in dissolved form, as suspensions or/and as emulsions, optionally in combination with suitable carrier or/and auxiliary substances. Further, the active ingredients can also be diagnostic labeling substances, e.g. fluorescent substances, dyes or X-ray contrast agents.

Preferably, the active ingredient is present in the BGs in immobilized form, i.e. under physiological conditions the packaged active ingredient remains within the EGs for a sufficient time to enable transport to the target cell or to the target tissue. The immobilization of the active ingredient can be effected by means of covalent or noncovalent interactions, e.g. electrostatic interactions, high-affinity biological interactions, by mechanical retention or a combination of two or more of said possibilities.

The immobilization of the active ingredient can be effected via direct or indirect interactions with a receptor which is located on the inside of the membrane, e.g. the inside of the cytoplasmic membrane, of the BGs as an integral membrane component or as a nonintegral membrane component anchored on the membrane. The receptor can for example be a heterologous polypeptide which is integrated into the cytoplasmic membrane of the BGs via one or more membrane anchors and is created in the bacterial cells by heterologous expression of corresponding fusion proteins which contain at least one membrane anchor domain and at least one receptor domain, e.g. avidin or streptavidin, before the lysis to the BGs.

Alternatively, it is also possible to anchor the receptor on the inside of the membrane only after lysis of the BGs, for example by the use of a receptor with two binding sites, wherein one binding site is capable of binding with high affinity to natural or recombinant structures on the inside of the membrane and the second binding site is available for the direct or indirect immobilization of active ingredients.

A receptor molecule located on the inside of the membrane of the BGs can effect direct or indirect immobilization of active ingredients in the interior of the BGs. In direct immobilization, a receptor is selected which can enter into an interaction with the active ingredient to be packaged into the BGs strong enough to cause substantial or complete retention of the active ingredient in the BG interior. For this, for example active ingredients modified with biotin, haptens or/and sugars, which can enter into a stable bond with receptors such as streptavidin, antibodies or lectins, can be used.

Alternatively, an indirect immobilization of the active ingredient onto the receptor, which is for example mediated via active ingredient-binding substances which also possess at least one additional binding site for the receptor, can also be effected. Examples of such active ingredient-binding substances are polymers, e.g. proteins such as polylysine or polysaccharides such as for example protamine sulfate or dextran. The active ingredient-binding substances also bear receptor-binding groups, e.g. biotin or biotin analogs, haptens or sugar groups capable of binding to lectins, which are able to effect anchoring onto the receptor located on the membrane.

Alternatively or/and in addition, the immobilization of the active ingredient can be effected via the formation of a matrix in the BG interior. This matrix is preferably a polymer matrix which is formed in situ in the interior of the ghost and which prevents outward diffusion of active ingredients from the BGs. The polymer matrix can be created by polymerization or/and copolymerization of suitable monomers or/and by co-deposition of aggregable substances in the interior of the BGs. The polymerization can be started by creation of appropriate conditions, e.g. by temperature increase, UV irradiation or/and addition of suitable initiators. It is advisable to use physiologically compatible monomers such as for example hydroxy fatty acids, amino acids, saccharides or derivatives thereof, which lead to the formation of a polymer degradable in the body under physiological conditions.

The preparation of the BGs modified with bacteriophages according to the invention according to the aforesaid aspect of the invention comprises firstly the preparation of the BGs by known methods, e.g. by transformation of the bacterial cell with a lysis gene, preferably the gene E of the phage PhiX174. The expression of the lysis gene in the bacterial cell is preferably effected by a regulable expression control sequence, for example by the temperature-regulable promoter/repressor system $\lambda$-pR/cI857. With this expression control system, the transformed bacteria are cultured at temperatures below 30° C. By increasing the temperature, preferably to $\geq$40° C., the heat-sensitive $\lambda$cI857 repressor is inactivated and the lysis gene expressed, which leads to the formation of a transmembrane tunnel structure in the cell envelope, whereby the cells are lysed within a few minutes. Using mutated $\lambda$/promoter/operator systems, culturing of the bacteria at higher temperatures, e.g. 37° C., is also possible (WO98/07874). The BGs can then be harvested by centrifugation and incubated with Bph under suitable conditions after washing and if necessary freeze-drying/reconstitution, so that adsorption of the Bph on the BG surface takes place. Before and/or after adsorption of the Bph, loading with active ingredients can be effected, wherein the BGs are contacted with a solution and/or suspension containing the active ingredient to be packaged under conditions which allow the penetration of sufficient quantities of active ingredient into the BGs. If necessary, receptor substances which enable immobilization of the active ingredient molecules on the inside of the membrane of the BGs or/and matrix-forming substances are also added. The addition of these substances can be effected before, simultaneously with or after the contacting of the BGs with the active ingredient to be packaged.

If the Bph binding to the bacteria requires a living cell, then the infection of the bacteria is effected before the induction of BG formation by lysis, e.g. E-mediated lysis. In addition, with filamentous Bph, it can be advantageous to allow the infection of the bacteria to proceed as far as the uptake of the coat proteins of the Bph in the cytoplasmic membrane and only thereafter to induce the E-mediated lysis. This allows the introduction of heterologous proteins into the cytoplasmic membrane of bacteria by a natural route since these are recycled in the normal infection cycle of the Bph and is an alternative to the already patented process of compartmentalization of recombinant polypeptides in host cells (WO 00/44878).

As well as their advantages for the targeting or the transport of active ingredients, the Bph can also serve for the establishment of desired physical properties, e.g. hydrophobicity or charge density, on the surface of bacterial ghosts. These properties can be established by the Bph loading level (number of phages per ghost) or by modifications of the Bph coat proteins (hydro-phobicity). In addition, Bph do not consist only of pure protein structures of different size and form, there are also lipid-coated Bph (e.g. PM2, PRD1, Bam35 and Phi6), which thus extend the spectrum for the surface modification of BGs.

The BGs modified with Bph according to the invention can be used as components of pharmaceutical compositions, e.g. as vaccines or adjuvants, or as carrier and/or targeting vehicles for active ingredients, whereby the active ingredients can be present in the BG and/or in the Bph.

The BGs according to the invention are outstandingly suitable as carrier and targeting vehicles, since owing to their nature as bacterial envelopes the BGs are already preferentially taken up by cells of the immune system. This targeting can be further improved by use of Bph-modified BGs with modified envelopes, i.e. BGs which bear target-specific surface molecules, i.e. specific for target cells or target tissue, on their membrane exterior or/and in the bacteriophage coats. The introduction of these target-specific molecules, such as for example antibodies, antibody fragments, specific ligands etc., can be effected by recombinant expression of corresponding fusion polypeptides in the bacterial cell before the lysis or in the bacteriophages or/and by attachment by means of a suitable receptor system (e.g. streptavidin/biotin).

The administration of phage-modified ghosts according to the invention is suitable for the prevention or/and the combating of all sorts of diseases, e.g. for the combating of diseases caused by pathogens such as viruses, bacteria, parasites or fungi, or for the prevention or/and for the combating of tumor or autoimmune diseases or for gene therapy. Here the phage-modified ghosts themselves or/and active ingredients contained therein can cause the desired therapeutic action. With active ingredient-loaded ghosts, active ingredients which cause their physiological action after transport into the target cell are used as active ingredients against the disease in question. The present invention also enables the administration of active ingredient combinations, i.e. the BGs can contain several different active ingredients or mixtures of different BGs optionally with different active ingredients can be used. Further, the administration of active ingredients via BGs can also be used for diagnostic purposes (imaging).

Particularly preferably, the BGs are derived from gram-negative bacteria which are for example selected from *Escherichia coli, Klebsiella, Salmonella, Pseudomonas, Vibrio, Actinobacillus, Haemophilus, Pasteurella, Bordetella* and *Helicobacter*. The selection of the bacteriophages is made on the basis of the bacterial species used, all gram-negative bacteria and their Bph being in principle suitable.

The administration of the Bph-modified BGs can be effected by standard methods, for example orally, aerogenically, e.g. intranasally, intraocularly, topically or parenterally, e.g. intramuscularly, intraperitoneally, intravenously or subcutaneously.

The administration of the ghosts is preferably effected by the same route as a natural infection of the organism with the pathogen also takes place. Thus BGs which are intended for combating pathogenic agents whose main entry site is the gastrointestinal tract (*E. coli, Salmonella, Vibrio* or *Helicobacter*) are administered orally. Ghosts from pneumonia pathogens which contain appropriate active ingredients, e.g. *Actinobacillus, Pasteurella, Pseudomonas* or *Haemophilus*, are preferably administered aerogenically.

The administration of Bph-modified BGs according to the invention, optionally loaded with active ingredients, is suitable not only for human medicine but also for veterinary medicine, in particular for the protective vaccination of domestic animals such as for example pigs, cows, etc.

The administration of active ingredients via Bph-modified BGs has many advantages compared to previous administration forms. Thus small quantities of active ingredient already suffice to obtain a strong effect. Moreover, target cell/tissue-specific administration of the active ingredients is possible. Owing to the BG envelopes already having an immunogenic action per se, an adjuvant action is attained. The active ingredient enclosed in the BG is protected from degradation by physiological processes, e.g. by enzymes such as proteases, nucleases or hydrolases. In addition, combination with other active ingredients is possible. Finally, the BGs can be inexpensively prepared and the active ingredients can be formulated simply and inexpensively.

Finally, the invention also relates to a pharmaceutical composition comprising a Bph-modified BG. The pharmaceutical composition according to the invention can be present in the form of normal pharmaceutical preparations, e.g. as a solution or suspension administrable by injection or aerogenically, as an oral preparation, e.g. as tablet, capsule or dragee, as a cream or ointment, etc. Furthermore, the composition can be present as a reconstitutable lyophilizate.

The composition according to the invention is obtainable by a process comprising the steps:
(a) preparation of Bph-infected bacteria, followed by E-mediated BG production,
(b) preparation of BGs and
(c) contacting of the BGs with a Bph under conditions which lead to adsorption of the Bph on the BGs.

On the basis of their dimensions Bph are nanoparticles. BGs which are infected with Bph are therefore carriers of nanoparticles. By metal adsorption onto Bph or other stated modifications of Bph, these can thus find use for example as electrical conductors.

The present invention will be further explained by means of the following example.

EXAMPLE 1

$4.3 \times 10^9$ *E. coli* NM522 particles were placed on soft agar plates. The plates respectively contained no bacterial ghosts or 1 mg/ml, 3 mg/ml or 7 mg/ml of bacterial ghosts (prepared in known manner by *E lysis* of *E. coli* NM522 cells).

The bacterial cells present in the soft agar plates were infected with the phage φX174 and the resulting phage titer was determined. In soft agar plates without addition of ghosts, a phage titer of $2 \times 10^{12}$ pfu/ml was found. In plates with 1 mg/ml ghosts, the phage titer was $1 \times 10^{12}$ pfu/ml. In plates with 3 mg/ml ghosts, the phage titer was $2 \times 10^{10}$ pfu/ml and in plates with 7 mg/ml ghosts, the phage titer was $3 \times 10^6$ pfu/ml.

The decrease in the phage titer in the presence of increasing quantities of bacterial ghosts means that the phage φX174 infects not only living bacterial cells but also bacterial ghosts.

The resulting phage-modified bacterial ghosts can be obtained from the soft agar plates by normal methods, e.g. by centrifugation.

The invention claimed is:
1. A bacteriophage (Bph)-modified bacterial ghost, comprising Bph bound to a bacterial ghost, wherein said bacterial ghost is obtainable by Bph binding to bacteria before or/and after E-induced bacterial lysis, wherein the bacterial lysis is induced by expression of the E gene of bacteriophage PhiX174 in the bacteria.

2. The bacterial ghost as claimed in claim 1, wherein the Bph are selected from one or more species of the families Styloviridae, Myoviridae, Podoviridae, Tectiviridae, Corticoviridae, Plasma-viridae, Microviridae, Inoviridae and Leviviridae.

3. The bacterial ghost as claimed in claim 2, wherein the Bph are selected from lambdoid Bph, filamentous phages, T phages and PhiX174 phages.

4. The bacterial ghost as claimed in claim 1, wherein the Bph contains an active ingredient heterologous to the bacterial ghost.

5. The bacterial ghost as claimed in claim 4, wherein the Bph contains a heterologous polypeptide.

6. The bacterial ghost as claimed in claim 5, wherein the heterologous polypeptide is selected from recognition polypeptides for cell receptors which enable deliberate introduction into desired cell types, docking polypeptides, immunogenic poly-peptides and combinatorial polypeptides.

7. The bacterial ghost as claimed in claim 4, characterized in that the Bph contains a heterologous nucleic acid.

8. The bacterial ghost as claimed in claim 7, characterized in that the heterologous nucleic acid comprises a DNA vaccine, a therapeutic RNA or a gene therapy vector.

9. The bacterial ghost as claimed in claim 1, wherein the bacterial ghost contains an active ingredient packaged in its interior.

10. The bacterial ghost as claimed in claim 9, wherein the active ingredient is selected from pharmacologically active ingredients and labeling substances.

11. The bacterial ghost as claimed in claim 9, wherein the active ingredient is present in the bacterial ghosts in immobilized form.

12. The bacterial ghost as claimed in claim 11, wherein the immobilization is effected via interactions with a receptor which is located on the inside of the membrane of the bacterial ghosts.

13. The bacterial ghost as claimed in claim 11, wherein the immobilization is effected via the formation of a matrix in the BG interior.

14. The bacterial ghost as claimed in claim 13, wherein the matrix is formed by polymerization or/and copolymerization of monomers in the BG interior.

15. The bacterial ghost as claimed in claim 1, wherein the bacterial ghost with bound Bph is contained in a pharmaceutical composition.

16. The bacteriophage (Bph)-modified bacterial ghost according to claim 1, wherein said bacteriophage (Bph)-modified bacterial ghost is obtainable by Bph binding to the bacteria after the bacterial lysis.

17. A method for producing a bacteriophage (Bph)-modified bacterial ghost, comprising binding bacteria with Bph before or/and after bacterial lysis wherein the bacterial lysis is induced by expression of the E gene of bacteria.

18. A bacteriophage (Bph)-modified bacterial ghost, obtainable by adhering Bph to receptor substances of the bacterial outer membrane or cell appendages before or/and after E-induced bacterial lysis wherein the bacterial lysis is induced by expression of the E gene of bacteria.

19. The bacteriophage (Bph)-modified bacterial ghost according to claim 18, wherein said cell appendages are flagellae or pili.

* * * * *